Figure 2:
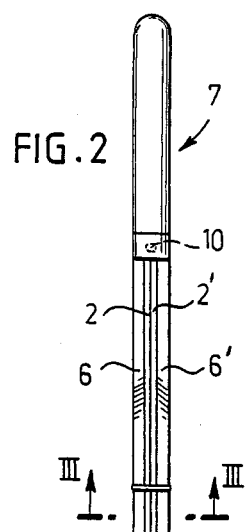

United States Patent [19]

Alasaarela

[11] Patent Number: 4,846,572
[45] Date of Patent: Jul. 11, 1989

[54] MOISTURE INDICATOR

[75] Inventor: Esko Alasaarela, Jokirinne, Finland

[73] Assignee: Moistic Oy, Oulu, Finland

[21] Appl. No.: 253,348

[22] Filed: Sep. 29, 1988

Related U.S. Application Data

[63] Continuation of Ser. No. 35,632, Apr. 7, 1987, abandoned.

[30] Foreign Application Priority Data

Sep. 30, 1986 [FI] Finland ............................. 863947

[51] Int. Cl.⁴ .............................................. G01N 21/00
[52] U.S. Cl. ......................................... 356/136; 73/73
[58] Field of Search .............. 356/136; 73/73, 290 R, 73/293, 323, 327, 334; 116/227

[56] References Cited

U.S. PATENT DOCUMENTS

| | | | |
|---|---|---|---|
| 2,943,530 | 7/1960 | Nagel . | |
| 3,026,718 | 3/1962 | Matson | 73/73 |
| 3,045,477 | 7/1962 | Matson | 73/73 |
| 3,345,870 | 10/1967 | Yoshinaga | 73/326 |
| 3,364,733 | 1/1968 | Holdsworth | 73/73 |
| 3,824,844 | 7/1974 | Strickland | 73/73 |
| 4,130,012 | 12/1978 | Lockerby et al. | 73/73 |

FOREIGN PATENT DOCUMENTS

| | | | |
|---|---|---|---|
| 2726082 | 12/1978 | Fed. Rep. of Germany | 73/293 |
| 2301013 | 9/1976 | France | 73/73 |
| 1158573 | 7/1969 | United Kingdom | 73/73 |
| 2152669 | 8/1985 | United Kingdom . | |

*Primary Examiner*—F. L. Evans
*Attorney, Agent, or Firm*—Michael N. Meller

[57] ABSTRACT

The invention relates to an optical device for measuring moisture in a substrate, in which device water is conveyed from the substrate along a porous absorption part (5) on a surface (4) of a prism so that is causes the critical angle of the total reflection to be changed thereon as a result of the change of the index of refraction. Another surface of the prism is dyed or patterned and covered in such a manner that it becomes visible only through reflection from the surface (4) when the surface is dry. When the surface (4) is moist, only the absorption part is visible through the viewing surface. The invention is advantageous in that due to the application of the principle of total reflection the change from an indication of the presence of moisture to an indication of the absence of moisture takes place sharply, not gradually.

6 Claims, 1 Drawing Sheet

MOISTURE INDICATOR

This application is a continuation, of application Ser. No. 035,632, filed 4/7/87, now abandoned.

The invention relates to an optical device for measuring moisture in a substrate of indoor plants or the like, the operation of the device being basd on the change of the critical angle of total reflection occurring at the interface between a clear optical material and air due to the influence of moisture.

Several rod-shaped devices have been suggested for indicating moisture in a substrate, in which devices the moisture rises to an absorption part positioned between shell parts due to the capillary phenomenon, and the moisture indication is made visible by means of a change taking place in the absorption part. U.S. Pat. Nos. 3,019,638 and 4,130,012 disclose a device the operation of which is based on the change of the colour of an absorbent paper used as an absorption part from a light blue to a dark blue when the paper gets moist. In the device disclosed in U.S. Pat. No. 3,824,844, the absorption part is white when it is dry, and it becomes nearly clear when it gets moist so that the colour behind it can be seen therethrough.

British Patent Application No. 2,059,077 discloses a device similar to that described above except that in place of paper the absorption part is formed by a hygroscopic material, such as calcium hydroxide, which is non-transparent in crystalline form (when dry) but transparent when it is in the form of a solution (i.e. moist). The absorption part in all the above-mentioned devices either changes colour or becomes partly colourless when it gets wet. A disadvantage thereof is the poor contrast. Even a slight drying causes the contrast between the moist and dry conditions to become obscure.

Finnish Patent Application No. 844,584 discloses a rod-like moisture indicator the operation of which is based on the change of the critical angle of the total reflection. The moisture rises therein due to the capillary phenomenon either in thin slits or in a porous core material. The application also discloses the use of a prism structure connected to a multi-part capillary tube system, whereby light is reflected back from a dry prism according to the principle of a prism reflector, while no reflection occurs with a moist prism. A disadvantage of this structure is that the use of indication colours is restricted and a striped indication is unclear.

U.S. Pat. No. 2,943,530 discloses an optical device for the indication of a liquid surface, which device is based on the change of the index of refraction of light on the surface of a prism when the liquid surface falls below the indication surface of the prism. The optical indication visible on another surface of the prism changes.

In the device according to the invention, the latter principle is utilized for measuring moisture in a substrate so that a distinct improvement is obtained with respect to the disadvantages mentioned above. An advantage of the invention is that due to the application of the principle of total reflection the change from an indication of the presence of moisture to an indication of the absence of moisture takes place sharply, not gradually. The invention is characterized in that the optical material effecting the moisture indication is made in the form of a prism having a first side which is left uncovered to form a viewing surface, a second side to which moisture is conveyed through a porous absorption part, and a third side which is dyed or patterned to be clearly distinguishable from the colour of the absorption part and which is covered with a covering colour, the angles of the prism depending on the index of refraction of the material in such a way that when the second side is moist, the absorption part itself is visible through the viewing surface of the prism, while an image of the dyed or patterned surface of the third side is visible through the viewing surface as a result of a total reflection occurring on the second side when said second side is dry.

The device operates in such a way that water is conveyed from the measuring point along a porous material to make contact with one surface of the prism so that the critical angle of the total refraction of light on this surface is changed and the indication visible on another surface of the prism is likewise changed. The operation is based on the fact that the index of refraction at the interface between the optical material and air differs from the index of refraction at the interface between the optical material and water. Said optical material can be any suitable transparent clear material, for instance glass or acryl.

Figure 1:
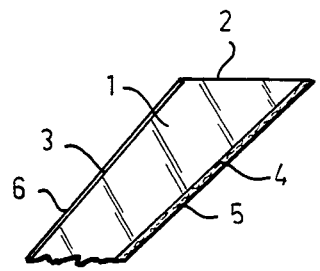
Figure 5:
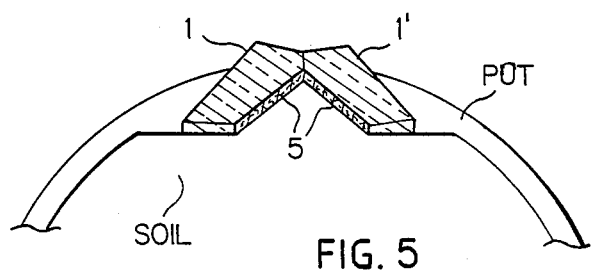
Figure 3:
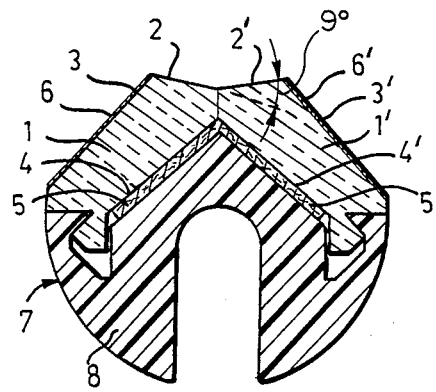
Figure 4:
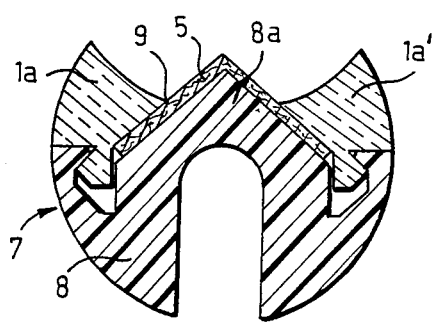

In the following the invention will be described in detail with reference to the drawings, wherein FIG. 1 illustrates the operating principle of a prism used in the invention, FIG. 2 illustrates the structure of the device according to the invention as seen from the viewing side, FIG. 3 is an enlarged cross-sectional view in the area of the indication surface along line III—III in FIG. 2, FIG. 4 is an enlarged cross-sectional view in the area of the absorption part along line IV—IV in FIG. 2, and FIG. 5 is a partial sectional view of the moisture indicator incorporated in a flower pot in accordance with the invention.

A first side of a prism 1, i.e. a viewing surface 2, is entirely visible; a second side, i.e. a moisture indicating surface 4 is covered by a porous absorption part 5; and a third surface, i.e. a surface 3, which is visible when absorption part 5 is dry, is covered with a covering colour 6. Light coming to the prism through the viewing surface undergoes a total reflection at the surface 4 when the absorption part 5 is dry, so that an image of the surface 3, indicating absence of moisture, can be seen by the observer through the viewing surface as a reflection from the surface 4. When the absorption part 5 is moist, no total reflection occurs at the surface 4 so that the absorption part itself is seen by the observer through the viewing surface. The angles of the prism 1 depend on the index of refraction of the prism material. For acryl, for instance, the index of refraction of which is 1.49, a suitable sharp angle is 6° and the other angles 132° and 42°. With these angle are values, the total reflection occurring between the prism material and air on the viewing surface 2 causes that the surface 3 for indicating absence of moisture can be seen through the viewing surface at any viewing angle only through reflection from the surface 4, when the surface 4 is dry. The limits of the viewing angle at which the surface 3 is visible through reflection from the surface 4 are an angle perpendicular to the surface on the left and an angle deviating about 30° from the right angle on the right. With wider angles, a total reflection occurs on the surface 4 also when the surface is moist. The angles can be dimensioned for other materials on the basis of the index of refraction. By varying the angles of the prism, it is also possible to affect the wideness of the usable viewing angle.

FIG. 2 shows the moisture indicating device 7 operating on the prism principle as seen in the direction facing the viewing surface 2. The device comprises two prisms 1 and 1' which are attached opposite to each other as shown in FIG. 3. The viewing angle at which either of the prisms shows a surface 6 and 6' indicating absence of moisture, when surfaces 4 and 4' are dry, is altogether about 60°. The viewing surface 2 and 2' of the prisms are arranged at a relative angle of 9° from parallel, so that at a viewing angle of 90°, both surfaces are made to indicate absence of moisture at the same time, which makes the indication more intense. A body 8 presses the absorption parts 5 and 5' tightly against the prism surfaces 4 and 4'. The absorption parts 5 and 5' are formed by a strip made of a porous material (such as filter paper made of a glass fibre material). One end of the strip protrudes from an absorption opening 9 of the body to make contact with a substrate the moisture of which is to be determined. The moisture is evaporated into the air at the other end of the body through a small evaporation opening 10 positioned behind the rod.

Covering colour layers 6 and 6' cover those surfaces of the prism which have a colour (e.g. red) clearly distinct from the colour of the absorption part. The point 11 of the rod is so shaped that it cuts the substrate and presses the earth efficiently against the absorption part.

FIG. 4 shows a cross-sectional view of the rod in the area of the absorption opening. A body part 8a lifts up an absorption part 5 and extensions 1a and 1a' of the prism part press the absorption part into contact with the body part. The absorption part is thus maintained in place and makes good contact with the earth.

The moisture indicator according to the invention may also form an integral part of a flower pot (as shown in FIG. 5) so that the absorption part makes contact with the earth over the whole length thereof or the earth itself may function as an absorption part.

I claim:

1. An optical device for measuring moisture in a porous substrate such as soil, the operation of said device being based on the change of the critical angle of total reflection occurring at an interface between a clear optical material and air due to the presence of moisture, comprising:
    an extended body having an absorption opening at one end;
    porous strip-shaped absorption means having a first portion which communicates with said absorption opening;
    a layer of material having a surface appearance which contrasts with the surface appearance of said absorption material; and
    prism means made from said clear optical material, said prism means having a first surface which is exposed and serves as a viewing surface, a second surface which is in contact with a second portion of said absorption means different than said first portion and a third surface which opposes said layer of contrasting material,
    wherein the angles of said prism means are selected whereby when said second portion of said absorption means is moist, said second portion is visible through said first surface of said prism means due to the absence of total reflection at said second surface of said prism means, and when said second portion of said absorption means is dry, said layer of material is visible through said first surface of said prism means due to the presence of total reflection at said second surface of said prism means.

2. An optical device as defined in claim 1, wherein said device is rod-shaped and said extended body has a sharp end.

3. An optical device as defined in claim 1, wherein said prism means comprises first and second prisms attached to each other, said absorption means being arranged between said prisms and said extended body.

4. An optical device as defined in claim 1, wherein said extended body has an evaporation opening at an end opposite to said one end thereof, and said absorption means is in communication with said evaporation opening.

5. An optical device as defined in claim 3, wherein said prisms are made of acryl, the index of refraction of which is 1.49, the angles of each prism are 6°, 132° and 42°, and the angle between the respective viewing surfaces of said prisms is 9°.

6. An optical device as defined in claim 1, wherein said device is formed as an integral part of a flower pot, said device being arranged whereby when said flower pot is filled with a porous substrate, said absorption means communicates with said porous substrate by way of said absorption opening.

* * * * *